US011273046B2

(12) United States Patent
Dewey

(10) Patent No.: US 11,273,046 B2
(45) Date of Patent: Mar. 15, 2022

(54) SPINAL IMPLANT SYSTEM AND METHOD

(71) Applicant: WARSAW ORTHOPEDIC INC., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 91 days.

(21) Appl. No.: 16/866,996

(22) Filed: May 5, 2020

(65) Prior Publication Data
US 2021/0346167 A1 Nov. 11, 2021

(51) Int. Cl.
*A61F 2/44* (2006.01)
*A61F 2/30* (2006.01)

(52) U.S. Cl.
CPC ........ *A61F 2/44* (2013.01); *A61F 2002/3054* (2013.01); *A61F 2002/30266* (2013.01); *A61F 2002/30523* (2013.01); *A61F 2002/30579* (2013.01)

(58) Field of Classification Search
CPC .. A61F 2/44; A61F 2/4611; A61F 2/46; A61F 2/442; A61F 2002/30266; A61F 2002/30523; A61F 2002/3054; A61F 2002/30579
USPC .......................................... 623/17.11–17.16
See application file for complete search history.

(56) References Cited

U.S. PATENT DOCUMENTS

| 7,850,733 | B2 | 12/2010 | Baynham et al. | |
|---|---|---|---|---|
| 9,848,993 | B2 | 12/2017 | Moskowitz et al. | |
| 10,137,006 | B2 | 11/2018 | Dewey et al. | |
| 10,188,527 | B2 | 1/2019 | Rogers et al. | |
| 2017/0216045 | A1* | 8/2017 | Dewey ..................... | A61F 2/447 623/17.15 |
| 2017/0319352 | A1* | 11/2017 | Dewey ................... | A61F 2/4455 623/17.15 |
| 2018/0078385 | A1* | 3/2018 | Dewey ................... | A61F 2/4611 623/17.15 |
| 2018/0206999 | A1 | 7/2018 | Suddaby | |
| 2019/0110900 | A1 | 4/2019 | Suddaby | |

FOREIGN PATENT DOCUMENTS

WO 2019022976 A1 1/2019

* cited by examiner

*Primary Examiner* — Jessica Weiss
(74) *Attorney, Agent, or Firm* — Sorell, Lenna & Schmidt, LLP

(57) ABSTRACT

A spinal implant includes a chassis extending along a first axis and including a first thread. A first member extends along a second axis and is pivotably coupled to the chassis. A second member extends along a third axis between and is pivotably coupled to the chassis. A rack includes opposite top and bottom surfaces. A first spur is coupled to the first member such that the first spur engages the top surface. A second spur is coupled to the second member such that the second spur engages the bottom surface. An actuator includes second thread that engages the first thread such that rotation of the actuator move the implant between a first orientation in which the second and third axes extend parallel to the first axis and a second orientation in which the second and third axes extends at an acute angle relative to the first axis.

20 Claims, 4 Drawing Sheets

SPINAL IMPLANT SYSTEM AND METHOD

TECHNICAL FIELD

The present disclosure generally relates to medical devices for the treatment of musculoskeletal disorders, and more particularly to a spinal construct configured for disposal with spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior technologies.

SUMMARY

In one embodiment, a spinal implant is provided. The spinal implant includes a chassis extending along a first longitudinal axis between opposite first and second ends. The chassis comprises a body and spaced apart first and second extensions extending from the body. The body comprises a first mating part. A first member extends along a second longitudinal axis between opposite first and second ends. The first end of the first member is pivotably coupled to the first end of the chassis. A second member extends along a third longitudinal axis between opposite first and second ends. The first end of the second member is pivotably coupled to the first end of the chassis. A rack is positioned between the extensions. The rack includes opposite top and bottom surfaces. A first spur is coupled to the second end of the first member such that the first spur engages the top surface. A second spur is coupled to the second end of the second member such that the second spur engages the bottom surface. An actuator comprises a second mating part that engages the first mating part such that rotation of the actuator relative to the chassis translates the rack relative to the chassis along the first longitudinal axis to move the implant between a first orientation in which the second and third longitudinal axes extend parallel to the first longitudinal axis and a second orientation in which the second and third longitudinal axes extends at an acute angle relative to the first longitudinal axis.

In one embodiment, a spinal implant is provided. The spinal implant includes a chassis extending along a first longitudinal axis between opposite first and second ends. The chassis comprises a body and spaced apart first and second extensions extending from the body. The body comprises a first mating part. A first member includes a first vertebral engaging surface. The first member extends along a second longitudinal axis between opposite first and second ends. The first end of the first member is pivotably coupled to the first end of the chassis. A second member includes a second vertebral engaging surface. The second member extends along a third longitudinal axis between opposite first and second ends. The first end of the second member is pivotably coupled to the first end of the chassis. A rack is positioned between the extensions. The rack includes opposite top and bottom surfaces. A first spur is coupled to the second end of the first member such that the first spur engages the top surface. A second spur is coupled to the second end of the second member such that the second spur engages the bottom surface. An actuator comprises a second mating part that engages the first mating part. A distance between the vertebral engaging surfaces defines a height of the implant. Rotation of the actuator relative to the members translates the rack relative to the chassis along the first longitudinal axis such that the spurs rotate relative to the chassis and the rack to increase the height of the implant.

In one embodiment, a spinal implant is provided. The spinal implant includes a chassis extending along a first longitudinal axis between opposite first and second ends. The chassis comprises a body and spaced apart first and second extensions extending from the body. The body comprises a female thread. A first member extends along a second longitudinal axis between opposite first and second ends. The first end of the first member is pivotably coupled to the first end of the chassis. A second member extends along a third longitudinal axis between opposite first and second ends. The first end of the second member is pivotably coupled to the first end of the chassis. A rack is positioned between the extensions. The rack includes opposite top and bottom surfaces. The top surface extends at an acute angle relative to the bottom surface such that the rack is wedge-shaped. The top surface comprises a first series of teeth. The bottom surface comprises a second series of teeth. A first spur comprises a first gear that engages at least one of the series of first teeth. A second spur comprises a second gear that engages at least one of the series of second teeth. An actuator comprises a male thread that engages the female thread such that rotation of the actuator relative to the chassis translates the rack relative to the chassis along the first longitudinal axis to move the implant between a first orientation in which the second and third longitudinal axes extend parallel to the first longitudinal axis and a second orientation in which the second and third longitudinal axes extends at an acute angle relative to the first longitudinal axis. The first spur pivots relative to the first member and the rack as the implant moves between the first and second orientations. The second spur pivots relative to the second member and the rack as the implant moves between the first and second orientations.

BRIEF DESCRIPTION OF THE DRAWINGS

The present disclosure will become more readily apparent from the specific description accompanied by the following drawings, in which.

DETAILED DESCRIPTION

Figure 1:
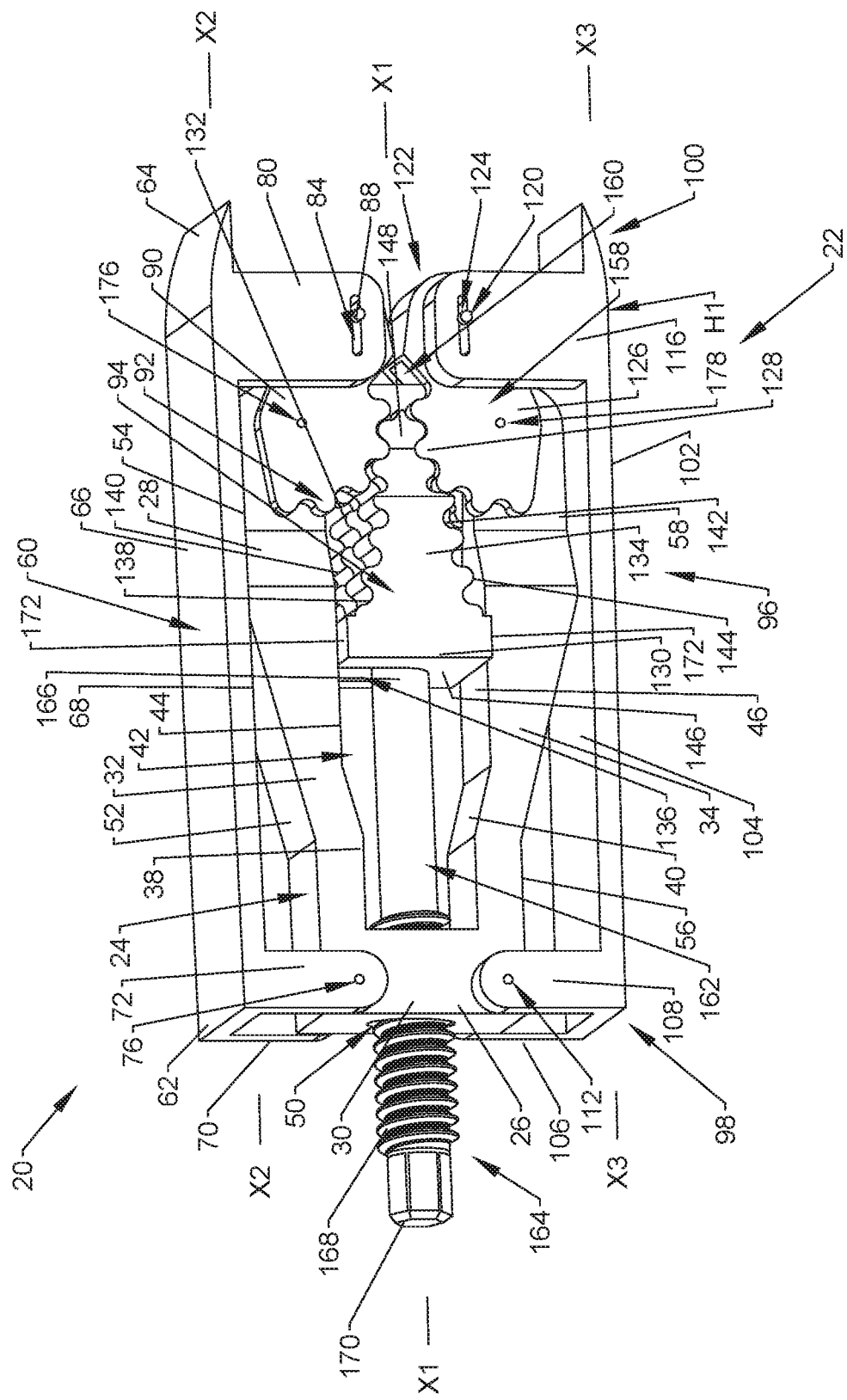
FIG. 1 is a perspective view of a spinal implant in accordance with the principles of the present disclosure.

The exemplary embodiments of a surgical system and related methods of use disclosed are discussed in terms of medical devices for the treatment of musculoskeletal disorders and more particularly, in terms of a spinal implant system that includes an expandable interbody implant configured for disposal with spaced vertebrae and a method for treating a spine.

In some embodiments, the expandable interbody implant includes a chassis, opposing endplates, a wedge-shaped rack, opposing spurs and a drive screw. In one embodiment, the rack pushes the spurs apart, increasing the total amount of expansion of the implant. In one embodiment, providing two spurs doubles the amount of expansion compared to implants that include only one spur. In one embodiment, providing two spurs and a wedge-shaped rack increases the total expansion of the implant compared to implants that include only one spur and a linear rack. In some embodiments, a spring is included to pull the endplates together during collapse.

In one embodiment, one or all of the components of the spinal implant system are disposable, peel-pack, pre-packed sterile devices used with an implant. One or all of the components of the spinal implant system may be reusable. The spinal implant system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The present disclosure may also be alternatively employed with procedures for treating the lumbar, cervical, thoracic, sacral and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there is illustrated components of a surgical system, such as, for example, a spinal implant system 20.

The components of spinal implant system 20 can be fabricated from biologically acceptable materials suitable for medical applications, including metals, synthetic polymers, ceramics and bone material and/or their composites. For example, the components of spinal implant system 20, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 20 may be employed with surgical procedures, such as, for example, corpectomy and discectomy, which include fusion and/or fixation treatments that employ implants, to restore the mechanical support function of vertebrae.

Spinal implant system 20 includes an expandable interbody implant 22. In some embodiments, implant 22 includes a core, such as, for example, a chassis 24. Chassis 24 extends along a longitudinal axis X1 between an end 26 and an opposite end 28. End 26 includes a body 30 extending perpendicular to axis X1 and spaced apart extensions 32, 34 that each extend from body 30 to a wall 36. Wall 36 extends perpendicular to axis X1. An inner surface 38 of extension 32 and an inner surface 40 of extension 34 define a cavity 42. Surface 38 includes a planar section 44 and surface 40 includes a planar section 46 that faces section 44. Sections 44, 46 each extend parallel to axis X1. In some embodiments, body 30 and wall 36 are positioned between extension 34 and extension 36 to prevent movement of extension 34 relative to extension 36, and vice versa. Body 30 defines a mating part, such as, for example, a female thread 48. Thread 48 defines a passageway 50 that is coaxial with axis X1. An outer surface 52 of extension 32 includes a planar section 54 and an outer surface 56 of extension 34 includes a planar section 58 opposite section 54. Sections 54, 58 extend parallel to axis X1. In some embodiments, section 44, section 46, passageway 50, section 54 and/or section 58 may be disposed at alternate orientations, relative to axis X1, such as, for example, transverse and/or other angular orientations such as acute or obtuse, and/or may be offset or staggered.

Implant 22 includes a member, such as, for example, an end plate 60 pivotably coupled to chassis 24. Plate 60 extends along a second longitudinal axis X2 between an end 62 and an opposite end 64. Plate 60 includes a vertebral engaging surface 66 and an inner surface 68 opposite surface 66. Surface 66 and/or surface 68 extend parallel to axis X2. In some embodiments, plate 60 is tapered toward end 64 to facilitate insertion of implant 22 into an intervertebral space, as discussed herein. In some embodiments, surface 66 may be rough, textured, porous, semi-porous, dimpled, knurled, toothed, grooved and/or polished to facilitate engagement with tissue. In some embodiments, surface 66 and/or surface 68 may be disposed at alternate orientations, relative to axis X2, such as, for example, transverse, perpendicular and/or other angular orientations such as acute or obtuse, co-axial and/or may be offset or staggered.

End 62 includes spaced apart flanges 70, 72 extending from surface 68. A pin 74 extends through flange 70 and into chassis 24 and a pin 76 extends through flange 72 and into chassis 24 to couple plate 60 to chassis 24 such that plate 60 is pivotable relative to chassis 24 about pins 74, 76. Pin 74 is coaxial with pin 76 such that pins 74, 76 define a pivot axis that extends perpendicular to axes X1, X2.

End 64 includes spaced apart extensions 78, 80 extending from surface 68. Extension 78 includes a slot 82 and extension 80 includes a slot 84. A spur 86 is positioned between extension 78 and extension 80 such that opposite outer surfaces of spur 86 directly engage inner surfaces of extensions 78, 80. One or more pins, such as, for example, a pin 88 extends through slots 82, 84 and spur 86 such that spur 86 is pivotable and/or rotatable relative to plate 60 about pin 88. In some embodiments, slots 82, 84 are elongated to allow pin 88 to translate within slots 82, 84 such that pin 88 moves between first ends of slots 82, 84 and opposite second ends of slots 82, 84 as implant 22 moves between a collapsed or unexpanded orientation and an expanded orientation, as discussed herein. In some embodiments, slots 82, 84 extend parallel to axis X2. In some embodiments, slots 82, 84 may be disposed at alternate orientations, relative to axis X2, such as, for example, transverse, perpendicular and/or other angular orientations such as acute or obtuse, and/or may be offset or staggered. Spur 86 includes a gear 90 having a plurality of teeth 92 configured to engage a rack 94 of implant 22 as rack 94 translates relative to chassis 24 along axis X1 to move implant 22 between the unexpanded and expanded orientations, as discussed herein.

Implant 22 includes a member, such as, for example, an end plate 96 pivotably coupled to chassis 24. Plate 96 extends along a second longitudinal axis X3 between an end 98 and an opposite end 100. Plate 96 includes a vertebral engaging surface 102 and an inner surface 104 opposite surface 102. Surface 102 and/or surface 104 extend parallel to axis X3. In some embodiments, plate 96 is tapered toward end 100 to facilitate insertion of implant 22 into an intervertebral space, as discussed herein. In some embodiments, surface 102 may be rough, textured, porous, semi-porous, dimpled, knurled, toothed, grooved and/or polished to facilitate engagement with tissue. In some embodiments, surface 102 and/or surface 104 may be disposed at alternate orientations, relative to axis X3, such as, for example, transverse, perpendicular and/or other angular orientations such as acute or obtuse, co-axial and/or may be offset or staggered.

End 98 includes spaced apart flanges 106, 108 extending from surface 104. A pin 110 extends through flange 106 and into chassis 24 and a pin 112 extends through flange 108 and into chassis 24 to couple plate 96 to chassis 24 such that plate 96 is pivotable relative to chassis 24 about pins 110, 112. Pin 110 is coaxial with pin 112 such that pins 110, 112 define a pivot axis that extends perpendicular to axes X1, X3.

End 100 includes spaced apart extensions 114, 116 extending from surface 104. Extension 114 includes a slot 118 and extension 116 includes a slot 120. A spur 122 is positioned between extension 114 and extension 116 such that opposite outer surfaces of spur 122 directly engage inner surfaces of extensions 114, 116. One or more pins, such as, for example, a pin 124 extends through slots 118, 120 and spur 122 such that spur 122 is pivotable and/or rotatable relative to plate 96 about pin 124. In some embodiments, slots 118, 120 are elongated to allow pin 124 to translate within slots 118, 120 such that pin 124 moves between first ends of slots 118, 120 and opposite second ends of slots 118, 120 as implant 22 moves between the collapsed or unexpanded orientation and the expanded orientation, as discussed herein. In some embodiments, slots 118, 120 extend parallel to axis X3. In some embodiments, slots 118, 120 may be disposed at alternate orientations, relative to axis X3, such as, for example, transverse, perpendicular and/or other angular orientations such as acute or obtuse, and/or may be offset or staggered. Spur 122 includes a gear 126 having a plurality of teeth 128 configured to engage rack 94 as rack 94 translates relative to chassis 24 along axis X1 to move implant 22 between the unexpanded and expanded orientations, as discussed herein.

Rack 94 is movably coupled to chassis 24 and spurs 86, 122 such that rack 94 translates relative to chassis 24 along axis X1 to pivot spur 86 relative to plate 60 and pivot spur 122 relative to plate 96 to move implant 22 between the unexpanded and expanded orientations. Rack 94 includes a body 130 and spaced apart legs 132, 134 that extend outwardly from body 130. Body 130 defines a cavity 136 configured for disposal of a component of implant 22, as discussed herein. A top surface 138 of rack 94 defines a plurality of teeth 140 that extend along the entire lengths of legs 132, 134. Teeth 140 are configured to engage teeth 92 as implant 22 moves between the unexpanded and expanded orientations. An opposite bottom surface 142 of rack 94 defines a plurality of teeth 144 that extend along the entire lengths of legs 132, 134. Teeth 144 are configured to engage teeth 128 as implant 22 moves between the unexpanded and expanded orientations. Surface 138 extends non-parallel, such as, for example, at an acute angle relative to surface 142 to provide rack 94 with a wedge-shape. That is, an end 146 of rack 94 has a height that is greater than an opposite end 148 of rack 94. In some embodiments, rack 94 is continuously tapered from end 146 to end 148. In some embodiments, rack 94 is progressively tapered from end 146 to end 148

In some embodiments, gear 90 includes spaced apart arms 150, 152 that define a gap 154 therebetween. A portion of end 54 is disposed in gap 154 such that teeth 92 along arm 150 engage teeth 140 along leg 132 and teeth 92 along arm 152 engage teeth 140 along leg 134. In some embodiments, gear 126 includes spaced apart arms 156, 158 that define a gap 160 therebetween. A portion of end 54 is disposed in gap 160 such that teeth 128 along arm 150 engage teeth 144 along leg 132 and teeth 128 along arm 152 engage teeth 144 along leg 134.

Implant 22 includes a drive screw, such as, for example an actuator 162 including an end 164 and an opposite end 166. End 164 includes a mating part, such as, for example, a male thread 168 that engages thread 50 such that actuator 162 is coaxial with axis X1 and rotation of actuator 162 relative to chassis 24 and plates 60, 96 in a first rotational direction, such as, for example, clockwise, translates rack 94 relative to chassis 24 and plates 60, 96 along axis X1 in the direction shown by arrow A in FIG. 2 such that teeth 92 engage teeth 140 to pivot spur 86 relative to plate 60 in the direction shown by arrow B in FIG. 2 to move plate 60 relative to axis X1 in the direction shown by arrow C in FIG. 2 and teeth 128 engage teeth 144 to pivot spur 122 relative to plate 96 in the direction shown by arrow D in FIG. 2 to move plate 96 relative to axis X1 in the direction shown by arrow E in FIG. 2 to move implant 22 from the collapsed or unexpanded orientation, shown in FIG. 1, to the expanded orientation, shown in FIG. 3. Rotation of actuator 162 relative to chassis 24 and plates 60, 96 in an opposite second rotational direction, such as, for example, clockwise, translates rack 94 relative to chassis 24 and plates 60, 96 along axis X1 in the direction shown by arrow F in FIG. 2 such that teeth 92 engage teeth 140 to pivot spur 86 relative to plate 60 in the direction shown by arrow D in FIG. 2 to move plate 60 relative to axis X1 in the direction shown by arrow E in FIG. 2 and teeth 128 engage teeth 144 to pivot spur 122 relative to plate 96 in the direction shown by arrow B in FIG. 2 to move plate 96 relative to axis X1 in the direction shown by arrow C in FIG. 2 to move implant 22 from the expanded orientation, shown in FIG. 3, to the collapsed or unexpanded orientation, shown in FIG. 3.

End 166 includes a drive, such as, for example, a bit 170 configured for disposal in a socket of a driver to rotate actuator 162 relative to chassis 24 and plates 60, 96. In some embodiments, bit 170 includes a hexalobe cross-sectional configuration configured for disposal in a socket having a hexalobe cross-sectional configuration. However, it is envisioned that bit 170 may include a square, triangular, polygonal, star cross sectional configuration configured engage a correspondingly shaped socket of a driver. End 166 directly engages rack 94 for disposal of end 116 in cavity 136 to couple actuator 162 to rack 94 such that actuator 162 is rotatable relative to rack 94 and translation of actuator 162 relative to chassis 24 and plates 60, 96 along axis X1 also translates rack 94 relative to chassis 24 and plates 60, 96 along axis X1. In some embodiments, end 166 can be variously connected with rack 94, such as, for example, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

In some embodiments, one or more springs could be included between the endplates and the chassis for biasing the implant in the closed position and/or to allow for driving of the implant closed upon collapse. Springs could also be provided between the spur gears and the chassis, biasing them towards the centerline.

In some embodiments, implant 22 includes a pin 176 extending through gear 90 and chassis 24 and a pin 178 extending through gear 126 and chassis 24. Gear 90 is pivotable and/or rotatable relative to chassis 24 about pin 176 such that pin 176 defines an offset pivot and gear 126 is pivotable and/or rotatable relative to chassis 24 about pin 178 such that pin 178 defines an offset pivot. In some embodiments, gear 90 pivots relative to chassis 24 about pin 176 and gear 126 pivots relative to chassis 24 about pin 178 as implant 22 moves between the collapsed or unexpanded orientation, shown in FIG. 1, and the expanded orientation, shown in FIG. 3. In some embodiments, the mechanical advantage of implant 22 is driven by the offset pivots defined by pins 176, 178, and/or the pivots defined by pins 88, 120. The distance between pin 88 and pin 176 and between pin 120 and pin 178 can be made larger for less mechanical advantage but more expansion, or shorter to get greater advantage. In some embodiments, pin 176 extends through an elongated slot 180 in chassis 24 and pin 178 extends through an elongated slot 182 in chassis 24, as shown in FIG. 4. Slots 180, 182 each extend perpendicular to axis X1. In some embodiments, pin 176 translates between opposite ends of slot 180 and pin 178 translates between opposite ends of slot 182 as implant 22 moves between the collapsed or unexpanded orientation, shown in FIG. 1, and the expanded orientation, shown in FIG. 3. In some embodiments, slot 180 and/or slot 182 may be variously shaped, such as, for example, circular, oval, oblong, triangular, square, polygonal, irregular, uniform, non-uniform, offset, staggered, undulating, arcuate, variable and/or tapered. In some embodiments, slot 180 and/or slot 182 may be disposed at alternate orientations, relative to axis X1, such as, for example, transverse, perpendicular and/or other angular orientations such as acute or obtuse, co-axial and/or may be offset or staggered.

Figure 2:
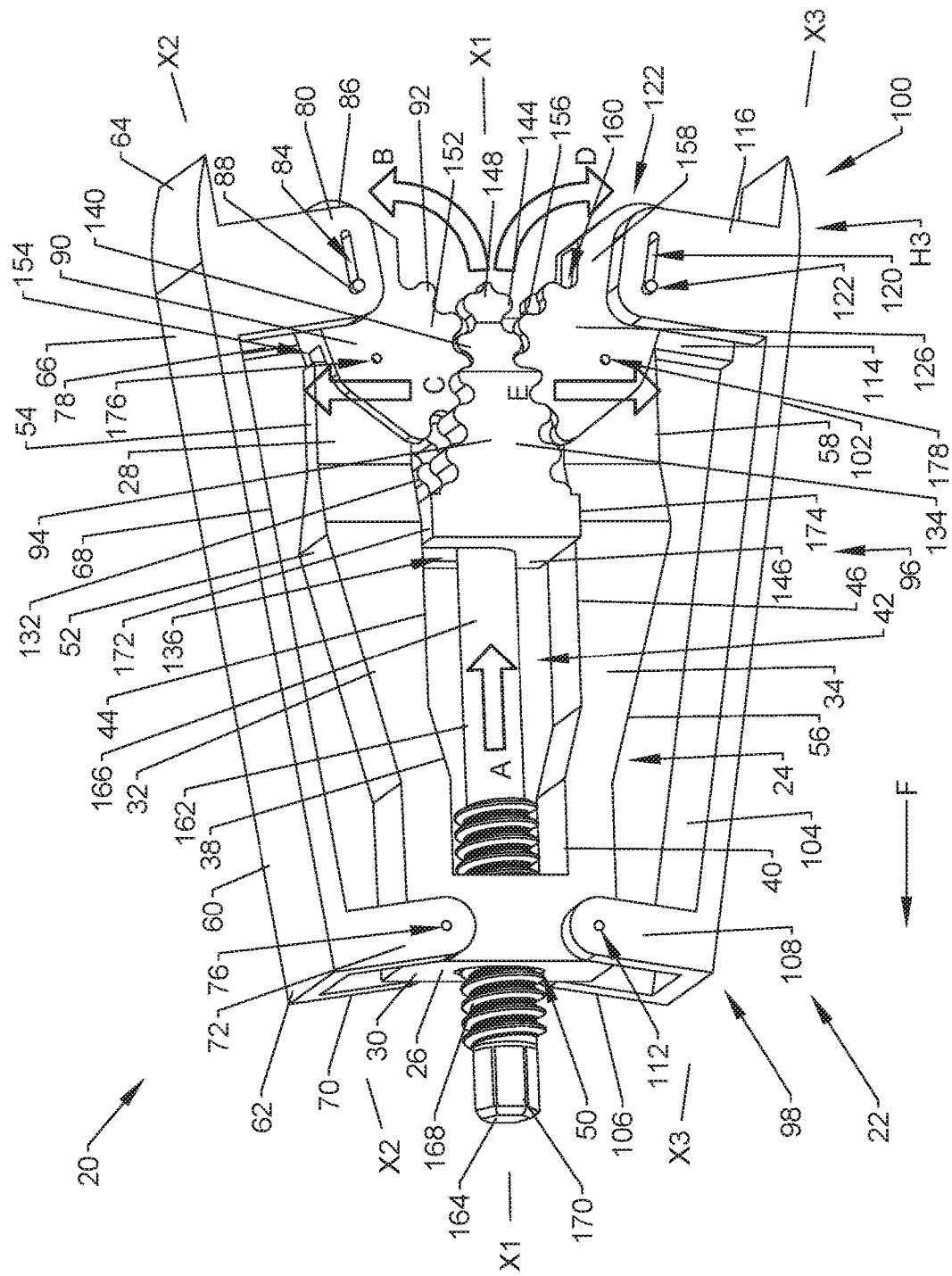
FIG. 2 is a perspective view of the implant shown in FIG. 1.

Implant 22 has a maximum height H1 when implant 22 is in the collapsed or unexpanded orientation shown in FIG. 1, wherein the maximum height of implant 22 is defined by the distance between surface 66 and surface 102. Implant 22 has a maximum height H2 when implant 22 is in the expanded orientation shown in FIG. 3, height H2 being greater than height H1. As implant 22 moves between the collapsed or unexpanded orientation shown in FIG. 1 and the expanded orientation shown in FIG. 2, implant 22 has a maximum height H3 that is greater than height H1 and less than height H2, as shown in FIG. 2. In some embodiments, pin 88 translates within slots 82, 84 and pin 124 translates within slots 118, 120 as implant 22 moves between the collapsed or unexpanded orientation shown in FIG. 1 and the expanded orientation shown in FIG. 3.

Figure 3:
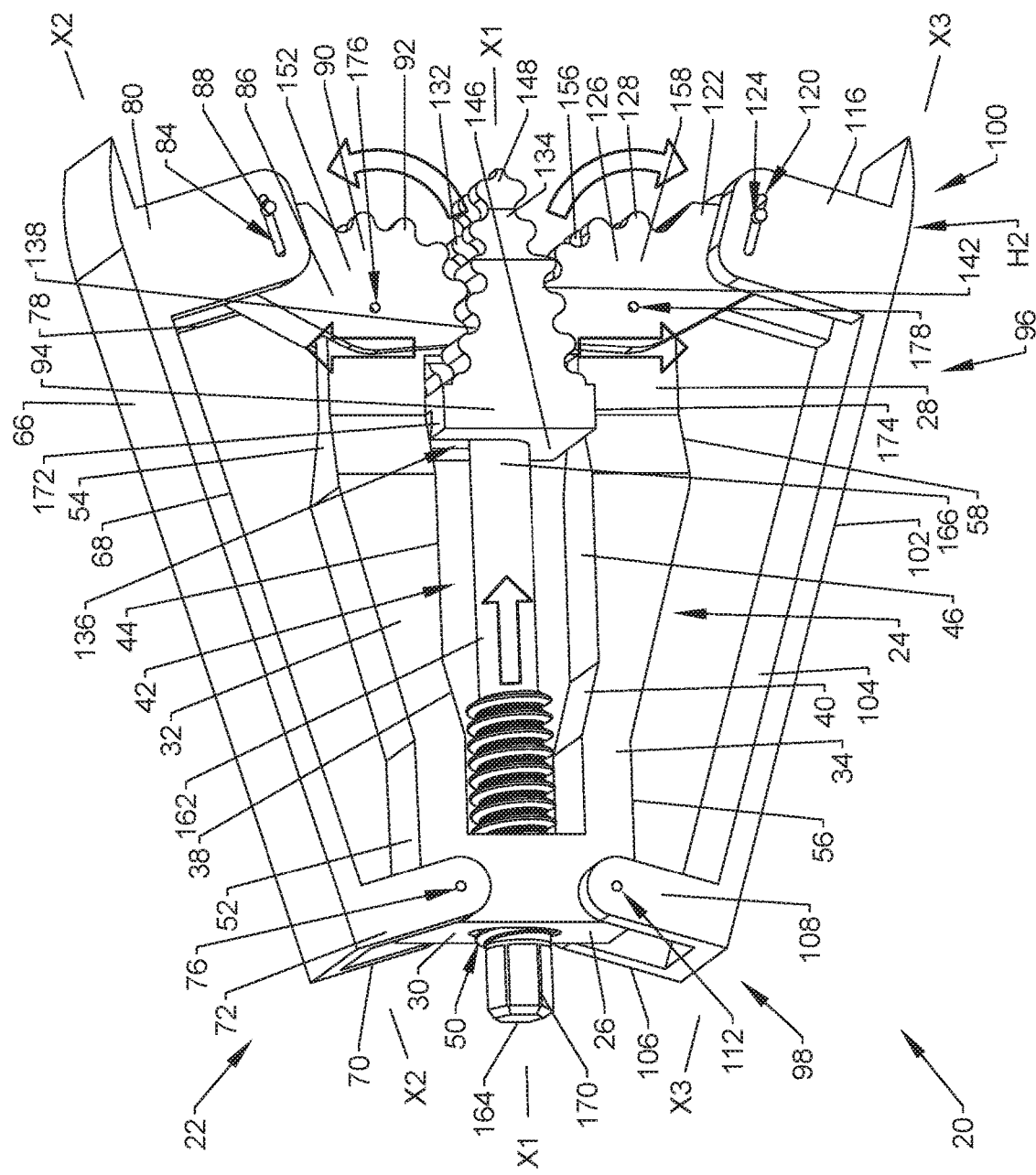
FIG. 3 is a perspective view of the implant shown in FIG. 1.
Figure 4:
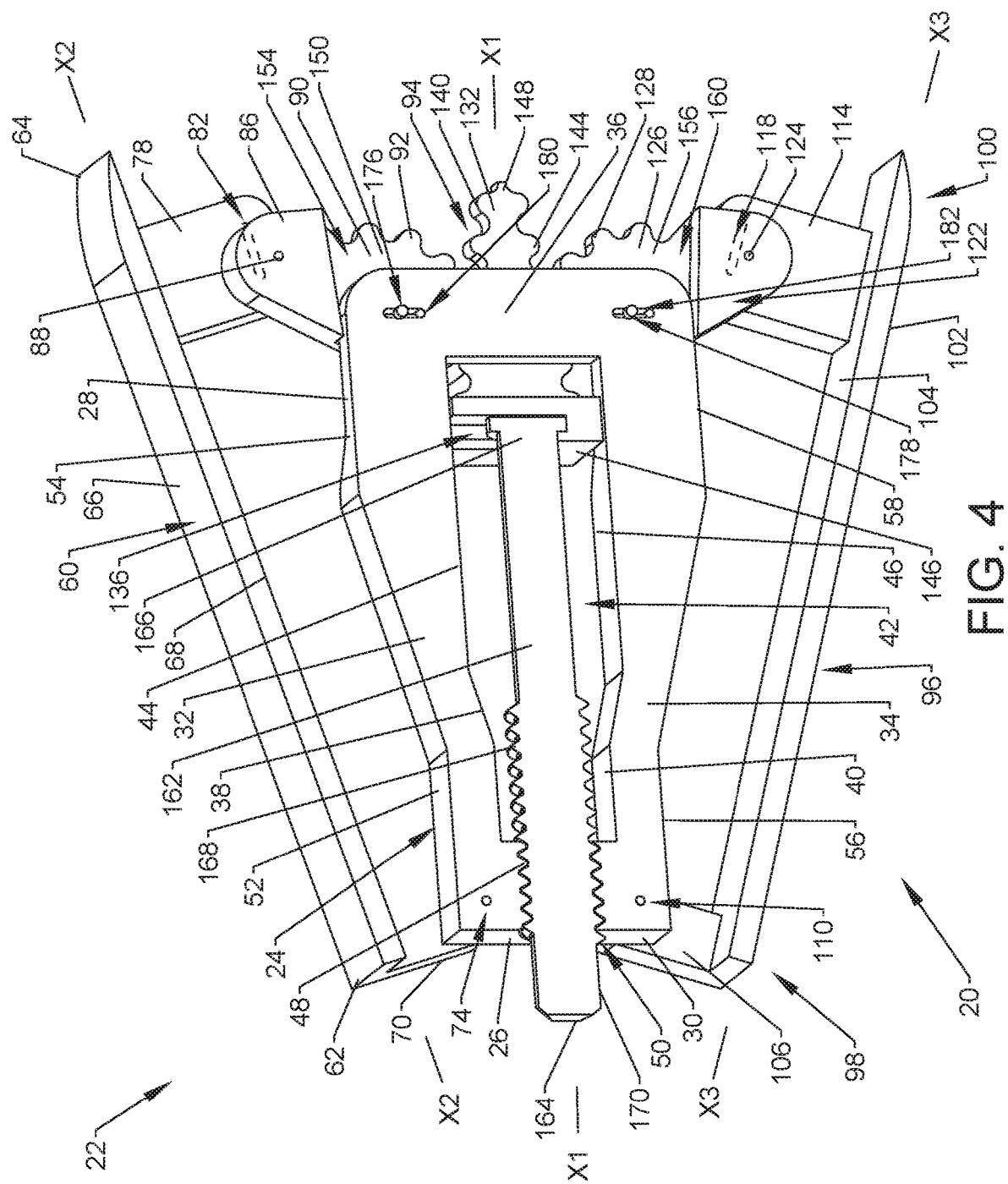
FIG. 4 is a perspective, cross-sectional view of the implant shown in FIG. 1.

In some embodiments, axes X2, X3 each extend parallel to axis X1 when implant 22 is in the collapsed or unexpanded orientation shown in FIG. 1 and axes X2, X3 each extend at an acute angle relative to axis X1 when implant 122 is in the expanded orientation shown in FIG. 3. In some embodiments, axes X2, X3 each extend an acute angle relative to axis X1 as implant 22 moves between the collapsed or unexpanded orientation shown in FIG. 1 and the expanded orientation shown in FIG. 3. In some embodiments, section 54 directly engages surface 68 and section 58 directly engages surface 104 when implant 22 is in the collapsed or unexpanded orientation shown in FIG. 1. In some embodiments, section 54 extends parallel to axes X1, X2 and section 58 extends parallel to axes X1, X3 when implant 22 is in the collapsed or unexpanded orientation shown in FIG. 1. In some embodiments, section 44 slides along a planar top surface 172 of body 130 and section 46 slides along a planar bottom surface 174 of body 130 as implant 22 moves between the collapsed or unexpanded orientation shown in FIG. 1 and the expanded orientation shown in FIG. 3. In some embodiments, surfaces 172, 174 each extend parallel to axis X1.

In assembly, operation and use, spinal implant system 20, similar to the systems and methods described herein, and including implant 22 is employed with a surgical procedure, such as, for example, a lumbar corpectomy for treatment of a spine of a patient including vertebrae. Spinal implant system 20 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of implant 22.

Spinal implant system 20 is employed with a lumbar corpectomy including surgical arthrodesis, such as, for example, fusion to immobilize a joint for treatment of an applicable condition or injury of an affected section of a spinal column and adjacent areas within a body. In some embodiments, implant 22 is configured for insertion within a vertebral space to space apart articular joint surfaces, provide support and maximize stabilization of vertebrae.

In use, to treat the affected section of vertebrae, a medical practitioner obtains access to a surgical site including vertebrae in any appropriate manner, such as through incision and retraction of tissues. In some embodiments, spinal implant system 20 may be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, corpectomy is performed for treating the spine disorder. The diseased and/or damaged portion of vertebrae, and diseased and/or damaged intervertebral discs are removed to create a vertebral space.

A preparation instrument is employed to remove disc tissue, fluids, adjacent tissues and/or bone, and scrape and/or remove tissue from a vertebral surface of a superior vertebra and/or a vertebral surface of an inferior vertebra. Implant 22 may be provided with at least one agent, similar to those described herein, to promote new bone growth and fusion to treat the affected section of vertebrae. The components of spinal implant system 20 may be completely or partially revised, removed or replaced. In some embodiments, implant 22 is employed to stabilize vertebrae as a pre-assembled device or can be assembled in situ.

Implant 22 is inserted into a vertebral space via a posterior approach, with implant 22 in the collapsed or unexpanded orientation shown in FIG. 1. A driver is coupled to bit 170 by inserting bit 170 into a socket of the driver. The driver rotates actuator 162 to move implant 22 from the collapsed or unexpanded orientation, shown in FIG. 1, to the expanded orientation, as shown in FIG. 3.

In some embodiments, implant 22 may be moved from the collapse or unexpanded orientation to the expanded orientation until surface 66 directly engages an end plate of a superior vertebra and surface 102 directly engages an end plate of an inferior vertebra. In some embodiments, a material, such as, for example, bone graft material is inserted through into implant 22.

In some embodiments, implant 22 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 20 can be used with screws to enhance fixation. In some embodiments, spinal implant system 20 and any screws and attachments may be coated with an agent, similar to those described herein, for enhanced bony fixation to a treated area. The components of spinal implant system 20 can be made of radiolucent materials such as polymers. Radiomarkers may be included for identification under x-ray, fluoroscopy, CT or other imaging techniques.

In some embodiments, the height of implant 22 may be decreased by coupling the driver to implant 22, as discussed herein, and rotating the driver to move implant 22 from the expanded orientation, shown in FIG. 3, to the collapsed or unexpanded orientation, shown in FIG. 1.

In some embodiments, the use of microsurgical and image guided technologies may be employed to access, view and repair spinal deterioration or damage, with the aid of spinal implant system 20. Upon completion of the procedure, the non-implanted components, surgical instruments and assemblies of spinal implant system 20 are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a chassis extending along a first longitudinal axis between opposite first and second ends, the chassis comprising a body and spaced apart first and second extensions extending from the body, the body comprising a first mating part;
a first member extending along a second longitudinal axis between opposite first and second ends, the first end of the first member being pivotably coupled to the first end of the chassis;
a second member extending along a third longitudinal axis between opposite first and second ends, the first end of the second member being pivotably coupled to the first end of the chassis;
a wedge-shaped rack positioned between the extensions, the rack including opposite top and bottom surfaces;
a first spur coupled to the second end of the first member such that the first spur engages the top surface;
a second spur coupled to the second end of the second member such that the second spur engages the bottom surface; and
an actuator comprising a second mating part that engages the first mating part such that rotation of the actuator relative to the chassis translates the rack relative to the chassis along the first longitudinal axis to move the implant between a first orientation in which the second and third longitudinal axes extend parallel to the first longitudinal axis and a second orientation in which the second and third longitudinal axes extends at an acute angle relative to the first longitudinal axis.

2. The spinal implant recited in claim 1, wherein the top and bottom surfaces each extend at an acute angle relative to the first longitudinal axis.

3. The spinal implant recited in claim 1, wherein the rack pushes the first spur apart from the second spur as the implant moves between the first and second orientations.

4. The spinal implant recited in claim 1, wherein the first spur pivots relative to the top surface and the first member and the second spur pivots relative to the bottom surface and the second member as the implant moves between the first and second orientations.

5. The spinal implant recited in claim 1, wherein the top surface comprises a first series of teeth and the bottom surface comprises a second series of teeth, the first spur engaging at least one of the first series of teeth and the second spur engaging at least one of the second series of teeth as the implant moves between the first and second orientations.

6. The spinal implant recited in claim 1, wherein:
the top surface comprises a first series of teeth and the bottom surface comprises a second series of teeth;
the first spur comprises a first gear that engages at least one of the first series of teeth as the implant moves between the first and second orientations; and
the second spur comprises a second gear that engages at least one of the second series of teeth as the implant moves between the first and second orientations.

7. The spinal implant recited in claim 1, wherein:
the top surface comprises a first series of teeth and the bottom surface comprises a second series of teeth;
the first spur comprises a first gear that engages at least one of the first series of teeth to pivot the first spur relative to the first member and the rack as the implant moves between the first and second orientations; and
the second spur comprises a second gear that engages at least one of the second series of teeth to pivot the second spur relative to the second member and the rack as the implant moves between the first and second orientations.

8. The spinal implant recited in claim 1, wherein the first mating part is a female thread and the second mating part is a male thread.

9. The spinal implant recited in claim 1, further comprising:
a first pin extending into the first end of the first member and the chassis such that the first member is pivotable relative to the chassis about the first pin; and
a second pin extending into the first end of the second member and the chassis such that the second member is pivotable relative to the chassis about the second pin.

10. The spinal implant recited in claim 1, wherein the actuator is rotatably coupled to the rack.

11. The spinal implant recited in claim 1, wherein the actuator comprises a first end that includes the second mating part and an opposite second end, the second end of the actuator directly engaging the rack.

12. The spinal implant recited in claim 1, wherein:
the top surface comprises a first series of teeth and the bottom surface comprises a second series of teeth;
the first spur comprises a first gear that engages at least one of the first series of teeth to pivot the first spur relative to the first member and the rack as the rack translates relative to the chassis along the first longitudinal axis to increase the height of the implant; and
the second spur comprises a second gear that engages at least one of the second series of teeth to pivot the second spur relative to the second member and the rack as the rack translates relative to the chassis along the first longitudinal axis to increase the height of the implant.

13. The spinal implant recited in claim 1, wherein the rack includes spaced apart legs, the legs each being wedge-shaped.

14. A spinal implant comprising:
a chassis extending along a first longitudinal axis between opposite first and second ends, the chassis comprising a body and spaced apart first and second extensions extending from the body, the body comprising a first mating part;
a first member including a first vertebral engaging surface, the first member extending along a second longitudinal axis between opposite first and second ends, the first end of the first member being pivotably coupled to the first end of the chassis;
a second member including a second vertebral engaging surface, the second member extending along a third longitudinal axis between opposite first and second ends, the first end of the second member being pivotably coupled to the first end of the chassis;
a wedge-shaped rack positioned between the extensions, the rack including opposite top and bottom surfaces;

a first spur coupled to the second end of the first member such that the first spur engages the top surface;

a second spur coupled to the second end of the second member such that the second spur engages the bottom surface; and an actuator comprising a second mating part that engages the first mating part, wherein a distance between the vertebral engaging surfaces defines a height of the implant, and wherein rotation of the actuator relative to the first and second members translates the rack relative to the chassis along the first longitudinal axis such that the spurs rotate relative to the chassis and the rack to increase the height of the implant.

15. The spinal implant recited in claim 14, wherein rotation of the actuator relative to the chassis translates the rack relative to the chassis along the first longitudinal axis to move the implant between a first orientation in which the second and third longitudinal axes extends parallel to the first longitudinal axis and a second orientation in which the second and third longitudinal axes extend at an acute angle relative to the first longitudinal axis.

16. The spinal implant recited in claim 14, wherein the top and bottom surfaces each extend at an acute angle relative to the first longitudinal axis.

17. The spinal implant recited in claim 14, wherein the top surface comprises a first series of teeth and the bottom surface comprises a second series of teeth, the first spur engaging at least one of the first series of teeth and the second spur engaging at least one of the second series of teeth as the rack translates relative to the chassis along the first longitudinal axis to increase the height of the implant.

18. The spinal implant recited in claim 14, wherein:
the top surface comprises a first series of teeth and the bottom surface comprises a second series of teeth;
the first spur comprises a first gear that engages at least one of the first series of teeth as the rack translates relative to the chassis along the first longitudinal axis to increase the height of the implant; and
the second spur comprises a second gear that engages at least one of the second series of teeth as the rack translates relative to the chassis along the first longitudinal axis to increase the height of the implant.

19. The spinal implant recited in claim 14, wherein the rack is spaced apart from the first and second members by the chassis.

20. A spinal implant comprising:
a chassis extending along a first longitudinal axis between opposite first and second ends, the chassis comprising a body and spaced apart first and second extensions extending from the body, the body comprising a female thread;

a first member extending along a second longitudinal axis between opposite first and second ends, the first end of the first member being pivotably coupled to the first end of the chassis;

a second member extending along a third longitudinal axis between opposite first and second ends, the first end of the second member being pivotably coupled to the first end of the chassis;

a rack positioned between the extensions, the rack including opposite top and bottom surfaces, the top surface extending at an acute angle relative to the bottom surface such that the rack is wedge-shaped, the top surface comprising a first series of teeth, the bottom surface comprising a second series of teeth;

a first spur comprising a first gear that engages at least one of the series of first teeth;

a second spur comprising a second gear that engages at least one of the series of second teeth; and an actuator comprising a male thread that engages the female thread such that rotation of the actuator relative to the chassis translates the rack relative to the chassis along the first longitudinal axis to move the implant between a first orientation in which the second and third longitudinal axes extend parallel to the first longitudinal axis and a second orientation in which the second and third longitudinal axes extends at an acute angle relative to the first longitudinal axis, wherein the first spur pivots relative to the first member and the rack as the implant moves between the first and second orientations, wherein the second spur pivots relative to the second member and the rack as the implant moves between the first and second orientations.

* * * * *